(12) United States Patent
Wan et al.

(10) Patent No.: US 11,967,399 B2
(45) Date of Patent: Apr. 23, 2024

(54) METHOD AND SYSTEM FOR CALCULATING TUMOR NEOANTIGEN BURDEN

(71) Applicant: Shenzhen NeoCura Biotechnology Corporation, Shenzhen (CN)

(72) Inventors: Ji Wan, Shenzhen (CN); Yiming Shen, Shenzhen (CN); Jian Wang, Shenzhen (CN); Youdong Pan, Shenzhen (CN); Yi Wang, Shenzhen (CN); Qi Song, Shenzhen (CN)

(73) Assignee: Shenzhen NeoCura Biotechnology Corporation, Shenzhen (CN)

( * ) Notice: Subject to any disclaimer, the term of this patent is extended or adjusted under 35 U.S.C. 154(b) by 282 days.

(21) Appl. No.: 17/151,076

(22) Filed: Jan. 15, 2021

(65) Prior Publication Data
US 2022/0112556 A1 Apr. 14, 2022

(30) Foreign Application Priority Data
Oct. 14, 2020 (CN) .......................... 202011098269.X

(51) Int. Cl.
*G16B 40/00* (2019.01)
*C12Q 1/6881* (2018.01)
(Continued)

(52) U.S. Cl.
CPC .......... *G16B 40/00* (2019.02); *C12Q 1/6886* (2013.01); *G16B 20/20* (2019.02); *G16B 20/30* (2019.02); *C12Q 2600/156* (2013.01)

(58) Field of Classification Search
CPC ...... G16B 40/00; G16B 20/30; C12Q 1/6886; C12Q 1/6881; C12Q 2600/156
See application file for complete search history.

(56) References Cited

U.S. PATENT DOCUMENTS

2018/0291074 A1* 10/2018 Chan .................. C07K 16/2818
2021/0238689 A1*  8/2021 Cheung .................. G16B 20/20

OTHER PUBLICATIONS

Miller, A., et al. "High somatic mutation and neoantigen burden are correlated with decreased progression-free survival in multiple myeloma." Blood cancer journal 7.9 (2017): e612-e612. (Year: 2017) (Year: 2017).*

(Continued)

*Primary Examiner* — Russell S Negin
*Assistant Examiner* — Guozhen Liu
(74) *Attorney, Agent, or Firm* — Bayramoglu Law Offices LLC

(57) ABSTRACT

A method and a system for calculating tumor neoantigen burden (TNB) are provided. The method includes: step S1: processing a normal sample and a tumor sample, sequencing a specific region and detecting somatic mutations in the sample; step S2: annotating and filtering the somatic mutations, and translating to obtain mutant peptide sequences of a patient; step S3: filtering the mutant peptide sequences to obtain neopeptide sequences based on a proteome of the normal sample; step S4, performing a human leukocyte antigen (HLA) typing analysis based on alignment data of the normal sample to obtain HLA genotypes of the sample; step S5, predicting binding affinities between the neopeptide sequences and the HLA genotypes to obtain specific neoantigens of the sample, and performing a weighted scoring on each of the specific neoantigens and calculating the TNB of the sample.

4 Claims, 2 Drawing Sheets

(51) Int. Cl.
*C12Q 1/6886* (2018.01)
*G16B 20/20* (2019.01)
*G16B 20/30* (2019.01)
*C12Q 1/6869* (2018.01)

(56) References Cited

OTHER PUBLICATIONS

Nielsen, Morten, et al. "Immunoinformatics: predicting peptide-MHC binding." Annual Review of Biomedical Data Science 3 (2020): 191-215. (Year: 2020).*
Wu, Jingcheng, et al. "DeepHLApan: a deep learning approach for neoantigen prediction considering both HLA-peptide binding and immunogenicity." Frontiers in immunology 10 (2019): 2559. (Year: 2019).*
Shao, Xiaoshan M., et al. "High-throughput prediction of MHC class I and II neoantigens with MHCnuggets." Cancer immunology research 8.3 (2020): 396-408. (Year: 2020).*
Wood, Mary A., et al. "Burden of tumor mutations, neoepitopes, and other variants are weak predictors of cancer immunotherapy response and overall survival." Genome medicine 12 (2020): 1-16. Published: Mar. 30, 2020 (Year: 2020).*

\* cited by examiner

METHOD AND SYSTEM FOR CALCULATING TUMOR NEOANTIGEN BURDEN

CROSS REFERENCE TO THE RELATED APPLICATIONS

This application is based upon and claims priority to Chinese Patent Application No. 202011098269.X, filed on Oct. 14, 2020, the entire contents of which are incorporated herein by reference.

TECHNICAL FIELD

The present invention relates to the technical field of tumor immunotherapy, and in particular, to a method and a system for calculating tumor neoantigen burden.

BACKGROUND

Tumor immunotherapy provides a new method for tumor treatment. The immune checkpoint inhibitors, which reinvigorate antitumor immune responses by blocking immune-inhibitory pathways, have produced breakthrough therapeutic effects on many solid tumors. Similar to tumor-targeted therapy, the immune checkpoint inhibitors require specific molecular biomarkers to predict the effectiveness of treatment. Currently, commonly used molecular biomarkers related to the therapeutic effect of the immune checkpoint inhibitors include the expression level of PD-1/PD-L1, microsatellite instability (MSI), and tumor mutation burden (TMB). These molecular biomarkers can help to evaluate the therapeutic effect of the immune checkpoint inhibitors to some extent, clinically, however, there are still a large number of cases where the therapeutic effect is inconsistent with the threshold of existing molecular biomarkers.

In order to further improve the prediction accuracy of immune checkpoint inhibitors effectiveness, it is highly desirable to develop more accurate molecular biomarkers in clinical practice. Neoantigens are peptides generated by tumor cell-specific mutations, which can be identified by T cells. Compared with the mutations involved in TMB, which fails to consider the translation of the mutations and the patient's own human leukocyte antigen (HLA) subtypes, the molecular biomarkers derived from the patient's neoantigens can better reflect the activity of the immune system, so as to more accurately predict the therapeutic effect of the immune checkpoint inhibitors. Therefore, an evaluation method is urgently needed to measure tumor neoantigen burden.

SUMMARY

One of the objectives of the present invention is to provide a method for calculating tumor neoantigen burden (TNB), which can distinguish high- and low-quality neoantigens by performing a weighted scoring on each predicted neoantigen by taking into account information from different biological aspects, such as mutation quality, mutation frequency and binding affinity level, thus obtaining a value that can better reflect the real TNB of the sample.

The embodiment of the present invention provides a method for calculating tumor neoantigen burden (TNB), including:
step S1: processing a normal sample and a tumor sample, sequencing a specific region and detecting somatic mutations in the sample;
step S2: annotating and filtering the somatic mutations, and translating to obtain mutant peptide sequences of a patient;
step S3: filtering the mutant peptide sequences to obtain neopeptide sequences based on a proteome of the normal sample;
step S4, performing a human leukocyte antigen (HLA) typing analysis based on alignment data of the normal sample to obtain HLA genotypes of the sample;
step S5: predicting binding affinity between the neopeptide sequences and the HLA genotypes to obtain specific neoantigens of the sample, and performing a weighted scoring on each of the specific neoantigens and calculating the TNB of the sample.

Preferably, step S1: processing the normal sample and the tumor sample, sequencing the specific region and detecting somatic mutations in the sample, includes:
step S101: performing DNA sequencing on the normal sample and the tumor sample by whole-exome sequencing (WES) method or specific-region panel sequencing method, and performing an alignment on sequencing data to obtain a genome of the normal sample and a genome of the tumor sample;
step S102: obtaining somatic mutations in sequencing region of the sample from the genome of the normal sample and the genome of the tumor sample.

Preferably, step S2: annotating and filtering the somatic mutations, and translating to obtain mutant peptide sequences of the patient, includes:
step S201: annotating and filtering the somatic mutations, including removing synonymous mutations and intronic mutations;
step S202: performing a protein translation on filtered somatic mutations to obtain a mutant proteome of the sample;
step S203: applying sliding windows to the mutant proteome of the sample with a series of predetermined lengths to obtain candidate antigen peptides containing mutation sites of the sample, and the candidate antigen peptides are mutant peptide sequences.

Preferably, step S3: filtering the mutant peptide sequences to obtain neopeptide sequences based on the proteome of the normal sample, includes:
step S301: translating the the genome of the normal sample to obtain the proteome of the normal sample;
step S302: searching the candidate antigen peptides in the proteome of the normal sample, filtering a part existing in the proteome of the normal sample to obtain candidate neoantigen peptides of the sample.

Preferably, step S5: predicting the binding affinity between the neopeptide sequences and the HLA genotypes to obtain specific neoantigens of the sample, and performing the weighted scoring on each of the specific neoantigens and calculating the TNB of the sample, includes:
step S501: predicting the affinity between the neopeptide sequences and the HLA genotypes to obtain specific neoantigens of the sample;
step S502: performing a weight calculation on the specific neoantigens based on mutation annotation information, mutation frequency information and binding affinity to HLA genotype information, to obtain a weight value of each of the specific neoantigens;
step S503: accumulating the weight value of each of the specific neoantigens to calculate the TNB of the sample.

The present invention also provides a system for calculating tumor neoantigen burden (TNB), including:

a somatic mutation acquiring unit, wherein the somatic mutation acquiring unit is used to process a normal sample and a tumor sample, sequence a specific region and detect somatic mutations in the sample;

a candidate antigen peptide acquiring unit, wherein the candidate antigen peptide acquiring unit is used to annotate and filter the somatic mutations, and translate to obtain mutant peptide sequences of the sample;

a candidate neoantigen peptide acquiring unit, wherein the candidate neoantigen peptides acquiring unit is used to filter the mutant peptide sequences to obtain neopeptide sequences based on a proteome of the normal sample;

an HLA genotype acquiring unit, wherein the HLA genotype acquiring unit is used to perform a human leukocyte antigen (HLA) typing analysis based on alignment data of the normal sample to obtain HLA genotypes of the sample;

a TNB calculating unit, wherein the TNB calculating unit is used to predict binding affinities between the neopeptide sequences and the HLA genotypes to obtain specific neoantigens of the sample, and perform a weighted scoring on each of the specific neoantigens and calculate the TNB of the sample.

Preferably, the somatic mutation acquiring unit performs the following operations:

performing DNA sequencing on the normal sample and the tumor sample by whole-exome sequencing (WES) method or specific-region panel sequencing method, and performing an alignment on sequencing data to obtain a genome of the normal sample and a genome of the tumor sample;

obtaining somatic mutations in a sequencing region of the sample from the genome of the normal sample and the genome of the tumor sample.

Preferably, the candidate antigen peptide acquiring unit performs the following operations:

annotating and filtering the somatic mutations, including removing synonymous mutations and intronic mutations;

performing a protein translation on filtered somatic mutations to obtain a mutant proteome of the sample;

applying sliding windows to the mutant proteome of the sample with a series of predetermined lengths to obtain candidate antigen peptides containing mutation sites of the sample, wherein the candidate antigen peptides are mutant peptide sequences.

Preferably, the candidate neoantigen peptides acquiring unit performs the following operations:

translating the the genome of the normal sample to obtain a proteome of the normal sample;

searching the candidate antigen peptides in the proteome of the normal sample, filtering a part existing in the proteome of the normal sample to obtain candidate neoantigen peptides of the sample.

Preferably, the TNB calculating unit performs the following operations:

predicting binding affinities between the neopeptide sequences and the HLA genotypes to obtain specific neoantigens of the sample;

performing a weight calculation on the specific neoantigens based on mutation annotation information, mutation frequency information and binding affinity to HLA genotype information, to obtain a weight value of each of the specific neoantigens;

accumulating the weight value of each of the specific neoantigens to calculate the TNB of the sample.

Compared with the prior art, the solutions of the present invention have the following advantages.

1. In terms of the source of tumor neoantigen prediction, the present invention fully considers various possible neoantigen results, including but not limited to one type in prediction length, or limited to class I in HLA genotypes, so as to expand the screening range of neoantigens.

2. In terms of the calculation accuracy of tumor neoantigen burden, compared with the common method for simply calculating the number of the neoantigens to obtain the value of TNB, the present method can distinguish high-quality and low-quality neoantigens by performing a weighted scoring on each predicted neoantigen, and taking into account information from different biological aspects such as mutation quality, mutation frequency and binding affinity level, thus obtaining a value which can better reflect the real TNB of the sample.

Other features and advantages of the present invention will be described subsequently in the specification and, in part, will become apparent from the description or understood by the implementation of the present invention. The objectives and other advantages of the present invention can be achieved and obtained by the description, claims and the structure specially pointed out in drawings.

The technical solutions of the present invention are further described in detail below in conjunction with the drawings and embodiments.

BRIEF DESCRIPTION OF THE DRAWINGS

The drawings are used to provide a further understanding of the present invention and form a part of the specification. They are used to explain the present invention together with the embodiments of the present invention and do not constitute a limitation of the present invention. In the drawings.

DETAILED DESCRIPTION OF THE EMBODIMENTS

Preferred embodiments of the present invention will now be described with reference to the drawings. It should be understood that the preferred embodiments described herein are only used to illustrate and explain the present invention, and are not intended to limit the present invention.

Figure 1:
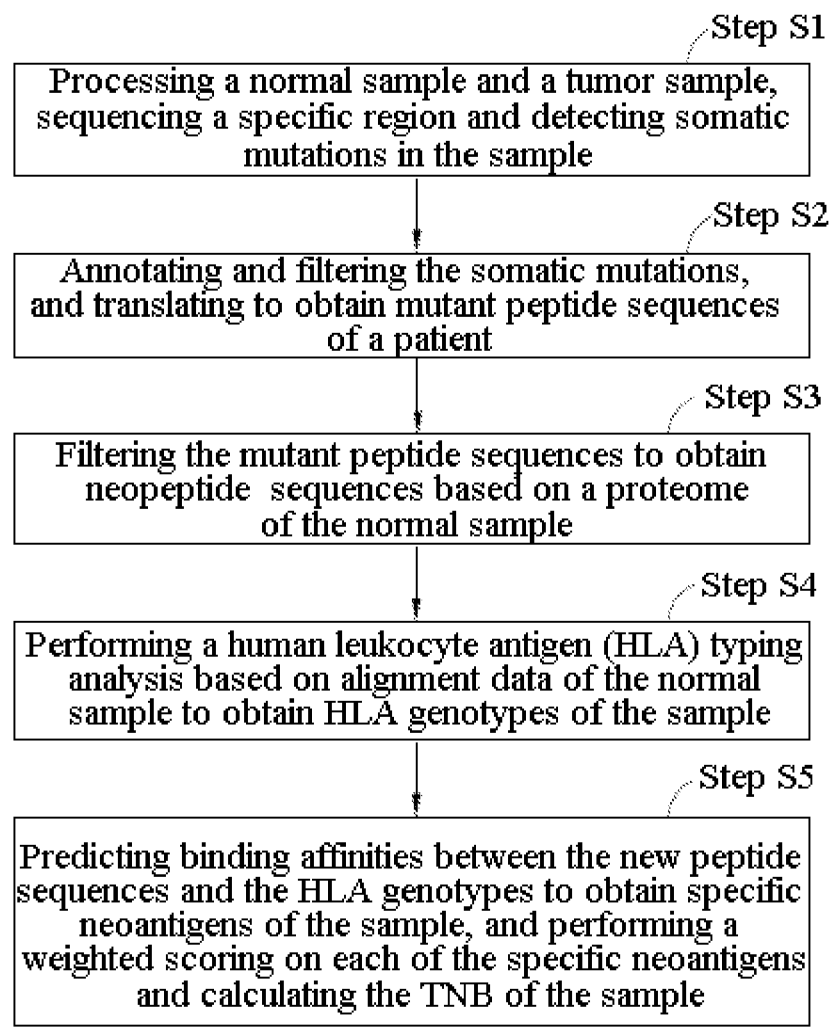
FIG. 1 is a schematic diagram showing a method for calculating tumor neoantigen burden in the embodiments of the present invention.
Figure 2:
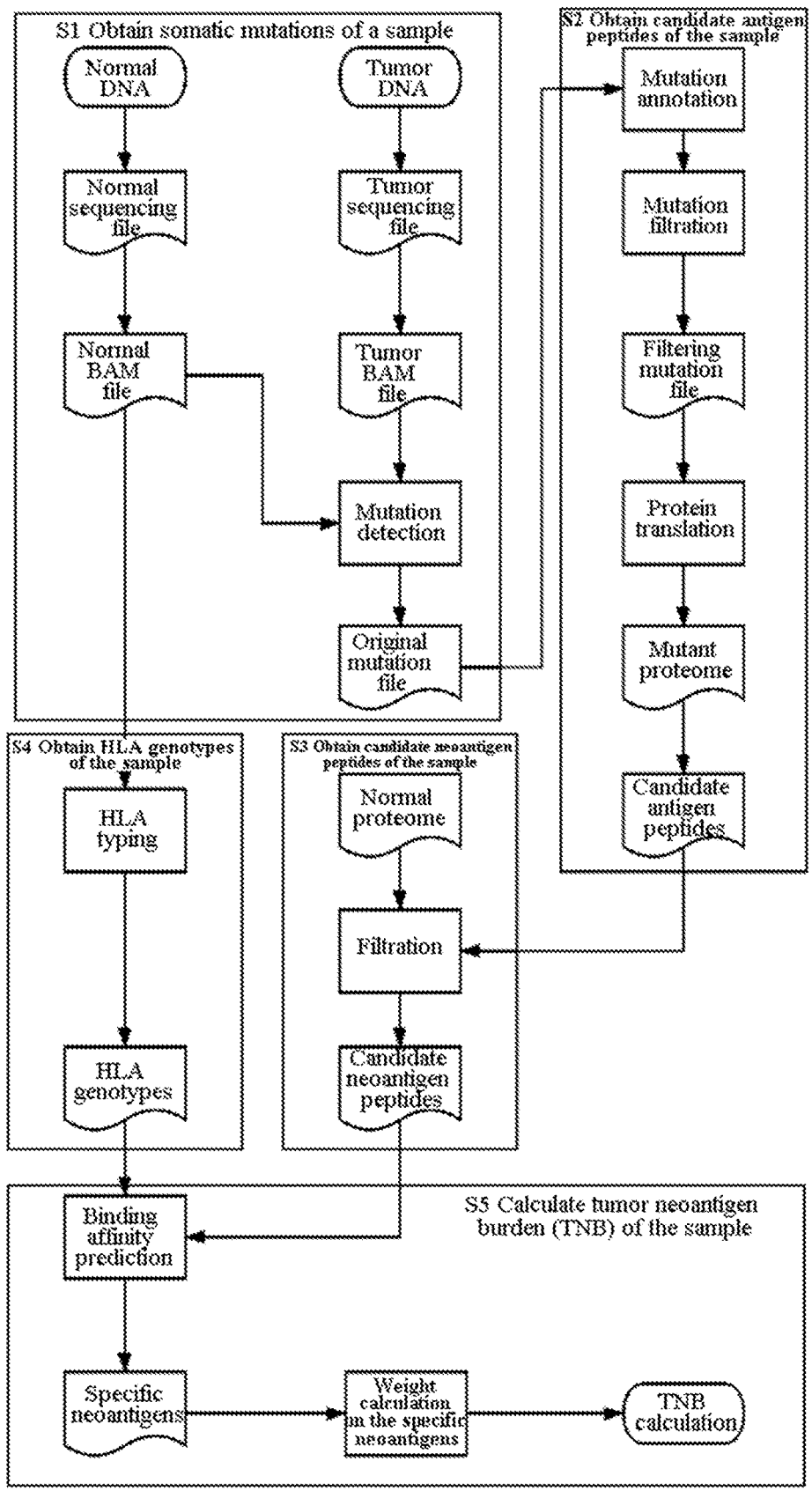
FIG. 2 is a flow diagram showing the method for calculating the tumor neoantigen burden in the embodiments of the present invention.

The embodiment of the present invention provides a method for calculating tumor neoantigen burden, as shown in FIG. 1, including the following steps.

Step S1: a normal sample and a tumor sample are processed, a specific region is sequenced and somatic mutations in the sample are detected.

Step S2: the somatic mutations are annotated and filtered, followed by translating to obtain mutant peptide sequences of a patient.

Step S3: the mutant peptide sequences are filtered to obtain neopeptide sequences based on a proteome of the normal sample.

Step S4, a human leukocyte antigen (HLA) typing analysis is performed based on alignment data of the normal sample to obtain HLA genotypes of the sample.

Step S5: binding affinities between the neopeptide sequences and the HLA genotypes are predicted to obtain specific neoantigens of the sample, then a weighted scoring is performed on each of the specific neoantigens and the TNB of the sample is calculated.

The working principle and advantages of the above-mentioned technical solution are as follows.

The TNB of the sample is calculated based on the weighted scoring of each of the specific neoantigens. To ensure the calculation accuracy of the final TNB, it is necessary to firstly ensure the prediction accuracy of the specific neoantigens. The present invention ensures the prediction accuracy of the specific neoantigens by four steps including integration, filtration, analysis, and prediction.

The method for calculating TNB of the present invention can distinguish high-quality and low-quality neoantigens by performing a weighted scoring on each predicted neoantigen, and taking into account information from different biological aspects such as mutation quality, mutation frequency and binding affinity level, thus obtaining a value that can better reflect the real TNB of the sample.

In one embodiment, step S1: a normal sample and a tumor sample are processed, a specific region is sequenced and somatic mutations in the sample are detected, which includes the following steps.

Step S101: DNA sequencing is performed on a normal sample and a tumor sample by whole-exome sequencing (WES) method or specific-region panel sequencing method, and then an alignment is performed on sequencing data to obtain a genome of the normal sample and a genome of the tumor sample.

Step S101 is to sequence and obtain a genome of the normal sample and a genome of the tumor sample, and the specific steps are as follows.

A DNA sequencing is performed on normal tissue and tumor tissue of the sample, and then an alignment is performed on sequencing data.

In this step, the main purpose is to obtain the genome of the normal sample and the genome of the tumor sample. Firstly, normal DNA data and tumor DNA data of the sample are sequenced to obtain a sequencing result files for subsequent analysis, and then the genome of the normal sample and the genome of the tumor sample are obtained based on the sequencing result files. The optional steps include but are not limited to quality filtering of sequenced reads, removing of adaptors and primers, etc.

Preferably, the genome of the normal sample and the genome of the tumor sample obtained in the present invention are subjected to the alignment based on DNA sequencing data with Burrows-Wheeler aligner (BWA).

Preferably, a FASTQ file obtained from the sequencing is aligned by BWA software to obtain a BAM file, and then the BAM file is subjected to duplicate removal and base quality score recalibration by GATK software.

Command line and parameters are as follows.

For alignment by BWA software, the example command is as follows:

```
bwa mem \
  -R '@RG\tID:sample\tLB:library\tSM:sample' \
  -t 10\
  -M bwa.index \
  reference.fa \
  in.1.fq in.2.fq
where:
-R represents a header file of an alignment result
```

```
-t represents the number of running threads
-M represents an index file used
reference.fa represents a FASTA file of a reference genome, and in.1.fq
and in.2.fq represent sequencing data
Deduplication by Picard software:
java -jar picard.jar \
  MarkDuplicates \
  I=in.bam \
  O=out.bam \
  M=picard1.txt
where:
I represents an input alignment file
O represents an output alignment file
M represents an output result statistics file
Base quality score recalibration (BQSR):
java -jar gatk.jar \
  BaseRecalibrator \
  -R reference.fa \
  -I input.bam \
  -O out.txt \
  --known-sites known.vcf \
where:
-R represents the file of the reference genome
-I represents an input BAM file
-O represents an output statistics result file
--known-sites represents a file of known mutations
```

Step S102: somatic mutations in a sequencing region of the sample are obtained from the genome of the normal sample and the genome of the tumor sample.

In this step, information of the somatic mutations and corresponding mutation frequency in tumor cells of the sample is obtained from an alignment file of the genome of the normal sample and the genome of the tumor sample.

Preferably, the somatic mutations are detected by Mutect2 tool of GATK software.

Command line and parameters are as follows.

```
Mutation detection by Mutect2:
java -jar gatk.jar Mutect2 \
  -R reference.fa \
  -I normal.bam \
  -I tumor.bam \
  -tumor tumor \
  -normal normal \
  -O sample.vcf
where:
-R represents the FASTA file of the reference genome
-I represents input alignment files
-tumor/-normal represents a name of a tumor/normal sample in the
alignment files
-O represents an output mutation file
```

In one embodiment, step S2: the somatic mutations are annotated and filtered, followed by translating to obtain mutant peptide sequences of the sample, which includes the following steps.

Step S201: the somatic mutations are annotated and filtered, including removing synonymous mutations and intronic mutations.

In this step, first, the somatic mutations in the sample obtained in S102 are annotated, including the annotation of the filtering information of the mutations, the annotation of the effect on protein function of the mutations, etc. Based on the annotation information, mutations occurring in the intron, mutations having no effect on the translated protein sequence, and the like can be removed.

Preferably, the obtained somatic mutations are annotated first to obtain filtering annotation information of each type of the mutations, such as mutation annotation with GATK FilterMutectCalls.

Preferably, all somatic mutations are annotated for the structural and functional effects of the protein sequence, e.g., using tools such as VEP.

Command line and parameters are as follows.

1. Annotation of the filtering information on the mutations by FilterMutectCalls:

```
java -jar gatk.j ar FilterMutectCalls \
-V sample.vcf \
-O sample.2.vcf
where:
-V represents an input mutation file
-O represents an output mutation file with a FILTER tag
2. Mutation annotation by VEP:
perl vep.pl \
-i in.vcf \
-o out.txt \
--assembly assembly \
--fork 10
where:
-I represents an input mutation file
-O represents an output result file
--assembly represents a version of the reference genome
--fork represents the number of threads
```

Step S202: protein translation is performed on filtered somatic mutations to obtain a mutant proteome of the sample.

In S202, based on the annotation result, the somatic mutations that do not produce protein sequence variation are filtered out. In the remaining result that can produce amino acid variation, codes are written according to genomic mutation information and detailed annotation information to construct mutant transcripts and translate the mutant transcripts into mutant protein sequences according to translation rules.

Step S203: the mutant proteome of the sample is cut by sliding windows with a series of predetermined lengths to obtain candidate antigen peptides containing mutation sites of the sample, and the candidate antigen peptides are mutant peptide sequences.

Codes are written to perform a sliding-window approach with a series of specific lengths on the mutant peptide sequences by combining the mutant peptide sequences obtained in S202 with the positions of mutant amino acids, to obtain a collection of the candidate neoantigen peptides. For example, in a mutant protein sequence, the position of the mutant amino acid is [m, n], and when treated with a length of 1, the maximum peptide starting position available is (m−1+1, n). In actual operation, the situation that the starting position (or termination position) of the peptides exceeds the position of the first (or last) amino acid on the protein sequence is timely filtered due to the relative position of the mutant amino acid on the protein and the setting of 1.

Preferably, a peptide length is 8-15 amino acids by default.

In one embodiment, step S3: the mutant peptide sequences are filtered to obtain neopeptide sequences based on a proteome of the normal sample, which includes the following steps.

Step S301: the the genome of the normal sample is translated to obtain a proteome of the normal sample.

Similarly, the proteome of the normal sample can be constructed based on a genome without somatic mutations according to the same translation rules.

Alternatively, release 98 published in Ensembl database is selected as a normal proteome of human.

Alternatively, a genome of normal sequencing data of the sample is selected to obtain the proteome of the normal sample according to the translation rules.

Step S302: the candidate antigen peptides are searched in the proteome of the normal sample, a part existing in the proteome of the normal sample is filtered to obtain candidate neoantigen peptides of the sample.

Codes are written to search the candidate antigen peptides of the sample obtained in step S2 in the proteome of the normal sample of a human, and to remove completely matched candidate peptides which can be found and keep candidate peptides which cannot be found completely matched, to obtain the candidate neoantigen peptides of the sample.

Step S4: a human leukocyte antigen (HLA) typing analysis is performed based on alignment data of the normal sample to obtain HLA genotypes of the sample. The specific steps are as follows.

S401, an HLA molecular typing is obtained based on the DNA sequencing data of the sample.

Preferably, a prediction of the HLA molecular typing is performed on the sequencing data of the sample by HLA-LA software, including the prediction results of class I and class II.

Command line and parameters are as follows:

```
HLA-LA.pl \
--BAM sample.bam \
--picard sam2fastq_bin picard-SamToFastq.jar \
--graph PRG_MHC_GRCh38_withIMGT \
--sampleID sample \
--maxThreads 10 \
--workingDir odir \
where:
--BAM represents an input alignment file
--picard_ sam2fastq_ bin represents SamToFastq tool of Picard software
--graph represents an HLA-LA reference map
--sampleID represents a sample name
--maxThreads represents the number of threads
```

In one embodiment, step S5: binding affinities between the neopeptide sequences and the HLA genotypes is predicted to obtain specific neoantigens of the sample, then a weighted scoring is performed on each of the specific neoantigens and the TNB of the sample is calculated, which includes the follow steps.

Step S501: the affinity between the neopeptide sequences and the HLA genotypes is predicted to obtain specific neoantigens of the sample.

Codes are written to perform binding affinities prediction of class I HLA and class II HLA on the candidate neoantigen peptides obtained in S3.

Step S502: a weight calculation is performed on the specific neoantigens based on mutation annotation information, mutation frequency information and binding affinity to HLA genotype information, to obtain a weight value of each of the specific neoantigens.

This step is based on the binding affinity prediction results in S501, aiming at the results with binding possibility shown in the prediction results. Codes are written to calculate a weight of each of the neoantigens by combining the mutation frequency information, mutation filtering information and the binding affinity to HLA. For example, different scores are marked for mutation frequency and neoantigens from different mutation frequency ranges. For example, different scores are marked for neoantigens with different mutation filtering information. For example, different scores are marked for rank results of the binding affinity prediction.

Finally, the weight score of each of the neoantigens is obtained by comprehensively calculating the scores of different characteristics of the neoantigens.

Step S503: the weight value of each of the specific neoantigens is accumulated to calculate the TNB of the sample.

The weight scores of all neoantigens of the sample are comprehensively calculated based on the results in S502 to obtain the TNB of the sample.

The present invention also provides a system for calculating tumor neoantigen burden (TNB), including:

a somatic mutation acquiring unit, wherein the somatic mutation acquiring unit is used to process a normal sample and a tumor sample, sequence a specific region and detect somatic mutations in the sample;

a candidate antigen peptide acquiring unit, wherein the candidate antigen peptide acquiring unit is used to annotate and filter the somatic mutations, and translate to obtain mutant peptide sequences of a patient;

a candidate neoantigen peptide acquiring unit, wherein the candidate neoantigen peptide acquiring unit is used to filter the mutant peptide sequences to obtain neopeptide sequences based on a proteome of the normal sample;

an HLA genotype acquiring unit, wherein the HLA genotype acquiring unit is used to perform a human leukocyte antigen (HLA) typing analysis based on alignment data of the normal sample to obtain HLA genotypes of the sample;

a TNB calculating unit, wherein the TNB calculating unit is used to predict binding affinities between the neopeptide sequences and the HLA genotypes to obtain specific neoantigens of the sample, and perform a weighted scoring on each of the specific neoantigens and calculate the TNB of the sample.

The working principle and advantages of the above-mentioned technical solutions are as follows.

The TNB of the sample is calculated based on the weighted scoring of each of the specific neoantigens. To ensure the calculation accuracy of the final TNB, it is necessary to firstly ensure the prediction accuracy of the specific neoantigens. The present invention ensures the prediction accuracy of the specific neoantigens by four steps including integration, filtration, analysis, and prediction.

The system for calculating TNB of the present invention can distinguish high-versus low-quality neoantigens by performing a weighted scoring on each predicted neoantigen, and taking into account information from different biological aspects such as mutation quality, mutation frequency and binding affinity level, thus obtaining a value which can better reflect the real TNB of the sample.

In one embodiment, the somatic mutation acquiring unit performs the following operations.

A DNA sequencing is performed on a normal sample and a tumor sample by a whole-exome sequencing (WES) method or a specific-region panel sequencing method, and an alignment is performed on sequencing data to obtain a genome of the normal sample and a genome of the tumor sample.

Somatic mutations in a sequencing region of the sample is obtained from the genome of the normal sample and the genome of the tumor sample.

In one embodiment, the candidate antigen peptide acquiring unit performs the following operations.

The somatic mutations are annotated and filtered, including removing synonymous mutations and intronic mutations.

Protein translation is performed on filtered somatic mutations to obtain a mutant proteome of the sample.

The mutant proteome of the sample is cut with a predetermined length to obtain candidate antigen peptides containing mutation sites of the sample, and the candidate antigen peptides are mutant peptide sequences.

In one embodiment, the candidate neoantigen peptides acquiring unit performs the following operations.

The the genome of the normal sample is translated to obtain a proteome of the normal sample.

The candidate antigen peptides are searched in the proteome of the normal sample, a part existing in the proteome of the normal sample is filtered to obtain candidate neoantigen peptides of the sample.

In one embodiment, the TNB calculating unit performs the following operations.

Binding affinities between the neopeptide sequences and the HLA genotypes are predicted to obtain specific neoantigens of the sample.

A weight calculation is performed on the specific neoantigens based on mutation annotation information, mutation frequency information and binding affinity to HLA genotype information, to obtain a weight value of each of the specific neoantigens;

The weight value of each of the specific neoantigens is accumulated to calculate the TNB of the sample.

Obviously, those skilled in the art can make various modifications and variations of the present invention without departing from the spirit and scope of the present invention. In this regard, if these modifications and variations of the present invention fall within the scope of claims of the present invention and the equivalent technologies, the present invention also intends to include these modifications and variations.

What is claimed is:

1. A method for calculating tumor neoantigen burden (TNB) and treating a tumor, comprising:

step S0: obtaining a normal tissue sample and a tumor tissue sample from a patient;

step S1: processing the normal tissue sample and the tumor tissue sample from the patient by sequencing a specific region and detecting somatic mutations in the patient;

step S2: annotating and filtering the somatic mutations to obtain filtered somatic mutations, and translating the filtered somatic mutations to obtain mutant peptide sequences of the patient;

step S3: filtering the mutant peptide sequences to obtain neopeptide sequences based on a proteome of the normal sample;

step S4, performing a human leukocyte antigen (HLA) typing analysis based on alignment data of the normal sample to obtain HLA genotypes of the patient;

step S5: predicting binding affinities between the neopeptide sequences and the HLA genotypes to obtain specific neoantigens of the patient, and performing a weighted scoring on each of the specific neoantigens and calculating the TNB of the patient, wherein the performing the weighted scoring on the patient comprises:

step S501: predicting the binding affinities between the neopeptide sequences and the HLA genotypes to obtain the specific neoantigens of the patient;

step S502: calculating a weight value of each of the specific neoantigens by combining mutation annotation information, mutation frequency information and binding affinities to HLA genotype information, wherein different scores are marked for neoantigen mutation frequency and neoantigens from different mutation frequency ranges, different scores are marked for neoantigens with different mutation filtering information, and different scores are marked for rank results of the neoantigen binding affinity prediction, then the weight value of each of the neoantigens is obtained by comprehensively calculating each of the different scores for each respective neoantigen, step S503: accumulating the weight value of each of the specific neoantigens by comprehensively calculating weight values of all of the neoantigens based on to obtain the TNB of the sample, and predicting a therapeutic effect of an immune checkpoint inhibitor on the tumor based on the weight value of each of the specific neoantigens, and administering an effective immune checkpoint inhibitor to treat the tumor in the patient based on the predicted therapeutic effect and calculated TNB of the sample.

2. The method according to claim 1, wherein, step S1: processing the normal sample and the tumor sample, sequencing the specific region and detecting the somatic mutations in the patient, comprises:

step S101: performing a DNA sequencing on the normal tissue sample and the tumor tissue sample by a whole-exome sequencing (WES) method or a specific-region panel sequencing method to obtain sequencing data, and performing an alignment on the sequencing data to obtain a genome of the normal sample and a genome of the tumor sample; and step S102: obtaining the somatic mutations in the specific region from the genome of the normal tissue sample and the genome of the tumor tissue sample.

3. The method according to claim 1, wherein, step S2: annotating and filtering the somatic mutations to obtain filtered somatic mutations, and translating the filtered somatic mutations to obtain the mutant peptide sequences of the patient, comprises:

step S201: annotating and filtering the somatic mutations, comprising removing synonymous mutations and intronic mutations, to obtain the filtered somatic mutations;

step S202: performing a protein translation on the filtered somatic mutations to obtain a mutant proteome of the patient; and step S203: applying sliding windows to the mutant proteome of the patient with a predetermined length to obtain candidate antigen peptides of the patient, wherein the candidate antigen peptides contain mutation sites, wherein the candidate antigen peptides are the mutant peptide sequences.

4. The method according to claim 3, wherein, step S3: filtering the mutant peptide sequences to obtain the neopeptide sequences based on the proteome of the normal tissue sample, comprises:

step S301: translating a genome of the normal tissue sample to obtain the proteome of the normal tissue sample; and step S302: searching the candidate antigen peptides in the proteome of the normal tissue sample, filtering a part existing in the proteome of the normal tissue sample to obtain candidate neoantigen peptides of the patient.

* * * * *